United States Patent
Hanger et al.

(10) Patent No.: US 9,232,803 B2
(45) Date of Patent: *Jan. 12, 2016

(54) CONTROL OF AAD DICOT VOLUNTEERS IN MONOCOT CROPS

(71) Applicant: DOW AGROSCIENCES LLC, Indianapolis, IN (US)

(72) Inventors: Gregory Hanger, Carmel, IN (US); Andrew E. Robinson, Brownsburg, IN (US); Norbert Satchivi, Westfield, IN (US); Terry R. Wright, Westfield, IN (US); Richard Chambers, Warriewood (AU)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/551,633

(22) Filed: Nov. 24, 2014

(65) Prior Publication Data

US 2015/0087518 A1  Mar. 26, 2015

Related U.S. Application Data

(63) Continuation of application No. 13/511,984, filed as application No. PCT/US2010/057998 on Nov. 24, 2010, now Pat. No. 8,916,751.

(60) Provisional application No. 61/263,950, filed on Nov. 24, 2009, provisional application No. 61/328,942, filed on Apr. 28, 2010.

(51) Int. Cl.
| | |
|---|---|
| *C12N 15/82* | (2006.01) |
| *C12N 15/87* | (2006.01) |
| *A01H 5/00* | (2006.01) |
| *A01N 57/20* | (2006.01) |
| *A01N 37/40* | (2006.01) |
| *A01N 43/40* | (2006.01) |
| *A01N 43/70* | (2006.01) |

(52) U.S. Cl.
CPC ............... *A01N 57/20* (2013.01); *A01N 37/40* (2013.01); *A01N 43/40* (2013.01); *A01N 43/70* (2013.01); *C12N 15/8274* (2013.01)

(58) Field of Classification Search
None
See application file for complete search history.

(56) References Cited

U.S. PATENT DOCUMENTS 8,722,410 B2 * 5/2014 Samuel et al. ................ 435/470

* cited by examiner

*Primary Examiner* — Shubo (Joe) Zhou
*Assistant Examiner* — Mykola Kovalenko
(74) *Attorney, Agent, or Firm* — James Daly, IV; Faegre Baker Daniels LLP

(57) ABSTRACT

The subject invention relates in part to the control of AAD-12 dicot volunteers in fields planted with monocot crops such as corn. The dicots can include soybeans and cotton.

9 Claims, No Drawings

CONTROL OF AAD DICOT VOLUNTEERS IN MONOCOT CROPS

CROSS REFERENCES

This application is a continuation of U.S. application Ser. No. 13/511,984, filed on Oct. 19, 2012, which is a national phase of PCT/US2010/057998, filed on Nov. 24, 2010, which claims the benefits of U.S. Provisional Application 61/328,942, filed on Apr. 28, 2010, and U.S. Provisional Application 61/263,950, filed on Nov. 24, 2009. The prior applications are incorporated into reference herein by reference in their entirety.

BACKGROUND

Corn (monocot) and soybeans (dicot), for example, can be rotated in various crop rotation cycles in various geographies. Cotton is also a dicot.

"Volunteer" plants are unwanted plants from the prior growing season that emerge in a field planted with crops for the current growing season. Volunteers are basically weeds, and can, like weeds, reduce harvest and yield of the crop of interest for the current growing season. The volunteers divert fertilizer resources and the like from the desired crops.

Unlike plain weeds, volunteers are often specifically engineered to be resistant to some herbicides. Thus, controlling volunteers can be more difficult than controlling naturally occurring weeds.

AAD (aryloxy alkanoate dioxygenase) genes as described herein impart high levels of tolerance to 2,4-D herbicides in plants that are transformed with an AAD gene.

AAD-1 genes also impart high levels of tolerance to phenoxy- and aryloxyphenoxyproplonate herbicides ("fops" such as fluazifop and haloxyfop). (AAD-1 genes are described in WO 2007/053482.) Thus, AAD-1 allows the use of some fops as either selection agents or as herbicides on crops where crop destruction would be expected without the AAD-1 gene.

AAD-12 and AAD-13 genes also impart high levels of tolerance to pyridyloxyacetate herbicides (such as triclopyr and fluroxypyr; "pyrs") to soybeans and other dicot species transformed with the gene. Thus, AAD-12 and AAD-13 each allow the use of pyrs as either selection agents or as herbicides on crops where crop destruction would be expected without the AAD-12 or AAD-13 gene.

There are very numerous dicot-only herbicides that kill dicots, or selective dicots.

BRIEF SUMMARY

The subject invention relates in part to the control of AAD-12 and/or AAD-13 dicot volunteers in fields planted with monocot crops such as corn. The dicots can include soybeans and cotton.

The subject invention also relates in part to the recognition that one potential downside to the use of AAD genes is that volunteers can be resistant to 2,4-D, as well as to pyrs (in the case of AAD-12 and AAD-13). Thus, in the case of AAD-12 or -13, pyr herbicides will no longer be effective for control of these volunteer AAD soybeans or cotton, for example, in fields planted with monocots such as corn. The subject invention relates in part to the recognition that when an AAD gene is stacked in dicots with other herbicide resistance traits (such as glyphosate, glufosinate, and the like), control of any resulting volunteer dicot plants in the following year can be an issue.

According to the subject invention, dicamba is selected, from almost innumerable other options, as being useful according to the subject invention for the control of volunteer AAD (such as AAD-12) dicot plants in a corn field.

In other embodiments, clopyralid is used for the control of volunteer AAD (such as AAD-12) dicot plants in a corn field.

Corn is naturally tolerant to both dicamba and clopyralid.

Yet another option for controlling volunteer AAD (such as AAD-12) dicots is triazines such as atrazine.

Another option according to the subject invention is if the dicots of the previous season were susceptible to either glyphosate or glufosinate, and the corn crop is tolerant to glyphosate or glufosinate, then glyphosate or glufosinate, respectively, could be used to control the dicot volunteers. Glyphosate could accordingly be used in a field of ROUND UP READY corn. Glufosinate could accordingly be used in a field of LIBERTY LINK corn. If the dicots of the previous season were susceptible to both glyphosate and glufosinate (that is, if the dicots did not have either resistance trait), and the corn crop is tolerant to both glyphosate and glufosinate, then either glyphosate or glufosinate or both could be used to control the dicot volunteers.

If the dicot (such as soy), however, comprises a PAT gene, for example, this would preclude the use of glufosinate to control the dicot volunteers (as the dicot PAT volunteers would tolerate glufosinate).

DETAILED DESCRIPTION

As used herein and unless otherwise specified, preferred dicots are soybeans or cotton.

One aspect of the subject invention includes the use of dicamba herbicides to remove volunteer AAD-12 or -13 dicots in a field of monocots, such as corn.

In some specific embodiments, the AAD-12 is present in soybeans as the AAD-12 soy event designated DAS-68416-4 having seed deposited with American Type Culture Collection (ATCC) with Accession No. PTA-10442, and progeny derived thereof. 2500 seeds were deposited in accordance with the Budapest Treaty on Oct. 22, 2009. The deposit was tested on Nov. 2, 2009, and on that date, the seeds were viable. Such events are disclosed in U.S. Ser. No. 61/263,950 (filed Nov. 24, 2009). Such AAD-12 dicot volunteers could be present in the following year's corn fields. Thus, the subject invention includes the application of a dicamba (or other as disclosed herein) herbicide to volunteer AAD-12 soy plants, particularly where the soybean plant comprises the 68416-4 event. Such "416" event plants comprise SEQ ID NO:1. AAD-12 protein sequences can be found in WO 2007/053482 (SEQ ID NO:2 and SEQ ID NO:4). AAD-13 protein sequences can be found in WO 2008/141154 (SEQ ID NO:2 and SEQ ID NO:4). Sequences for use in accordance with the subject invention can have at least 75%, 80%, 85%, 90%, 95%, or 99%, for example, sequence identity with any of these sequences.

Because of the specific detoxifying aspects of AAD genes, dicamba herbicides applied to corn fields would not be subject to detoxification by the AAD gene of the dicot volunteers, and AAD-12 or -13 dicot volunteers would remain highly susceptible to the dicamba herbicide.

According to the subject invention, various herbicide chemistries have been carefully selected to provide control of AAD-12 or -13 dicots as detailed herein. For example, when an AAD-12 or -13 gene was used alone in the previous season's dicot (such as soybeans), dicamba, clopyralid, atrazines, glyphosate, and/or glufosinate could be used to control volunteer AAD soybeans (or cotton), assuming that the soybeans (or other dicots) were naturally or engineered to be resistant to any of these herbicides.

That is, if the volunteer AAD-12 or -13 dicots were also stacked with a glyphosate- or glufosinate-trait, then glufosinate or glyphosate, respectively, could be used in the corn field of the current season, assuming that the corn also has a resistance trait against glufosinate or glyphosate, respectively.

Even if these AAD soybean volunteers possess glyphosate- and glufosinate-tolerance traits, dicamba (and/or the others) could still be used to control those volunteers.

Selection of herbicides to use on the current planted fields, according to the subject invention, can thus depend in part on the herbicide-tolerance trait(s) that were used in the previous season dicot, and on the tolerance trait(s) present in the field of corn (or other monocot) crop of the current growing season. Thus, additional herbicide chemistries can provide control of AAD-12 or -13 dicot volunteers.

In ROUNDUP READY (or GAT or other glyphosate-tolerant crops) or LIBERTY LINK (or other glufosinate-tolerant crops) corn fields, for example, glyphosate or glufosinate, respectively, can be used to control the AAD dicot volunteers, assuming the dicot volunteers do not also possess that same respective herbicide-tolerance trait. Again, a PAT gene in the soy (or other dicot) would preclude the use of glufosinate for controlling the soy (or other dicot) volunteers.

EXAMPLES

Example 1

Control of Volunteer AAD-12 Soybean in a Field Planted with AAD-1 Corn Using Alternative Herbicides In one embodiment, volunteer transgenic soybean lines containing the AAD-12 expression cassette are controlled within a field of AAD-1 corn by the application of a herbicide or combination of herbicides. The specific herbicide used to control the volunteer transgenic AAD-12 soybean line is dependent upon the type of AAD-1 corn seed being planted within the field (e.g., stacked with ROUNDUP READY (or GAT or other glyphosate-tolerant) trait, LIBERTY LINK (or other glufosinate-tolerant) trait, or other herbicide tolerant traits).

Furthermore, the AAD-12 trait may be stacked with other additional herbicide tolerant trait(s) via conventional breeding or a molecular stack. In such an example, the specific herbicide used to control the volunteer AAD-12 soybean stacked with another herbicide tolerant trait(s) will be dependent upon the additional herbicide tolerant trait(s) and the type of AAD-1 corn being planted within the field.

The application of a given herbicide can be made before planting at pre-emergence/burndown or post-emergence after planting to control the volunteer transgenic AAD-12 soybean lines. Table 1 lists the herbicides to be used at the different stages of planting (pre-emergence or post-emergence) to control volunteer transgenic soybean in a field planted with corn containing herbicide tolerant trait(s). Table 2 lists the herbicides to be used at different stages of planting to control volunteer AAD-12 soybean in a field planted with corn containing the AAD-1 herbicide tolerant trait. At or about a 1× Field Rate concentration of herbicide would be applied, as either a tank mix or alone, to the field for both pre-emergent and post-emergent volunteer control.

The control of transgenic soybean plants containing the AAD-12 expression cassette within a field of AAD-1 corn would be applicable for the control of volunteer AAD-12 transgenic dicot plants (including, but not limited too; soybean, cotton, canola, flax, sunflower, legumes, alfalfa, peanut, and tomato) within a field being planted with a monocot crop (including, but not limited too; corn, rice, sugar cane, switch grass, turf grass species, sorghum, barley, wheat, and oats, and durum). The example described above, in which volunteer transgenic AAD-12 soybean plants are controlled in an AAD-1 corn field, is illustrative of the invention and not intended to restrict the scope of this embodiment.

Example 2

Control of Volunteer Soybean (Conventional or Containing Non-AAD Herbicide Tolerance Traits) in a Field Planted with AAD Corn Using Alternative Herbicides In an embodiment, volunteer transgenic soybean lines (containing the Clear Field trait, Roundup Ready or other Glyphosate Tolerant Trait, Liberty Link Trait, Imidazolonine tolerant trait, or any stacked combination thereof) or volunteer conventional soybean lines are controlled within a field of transgenic AAD corn (either AAD-1 or AAD-12) by the application of a herbicide or combination of herbicides. The specific herbicide used to control the volunteer soybean plants is dependent upon the type of soybean seed being planted within the field (e.g., conventional soybean, Roundup Ready Soybean, Liberty Link Soybean, etc.).

Moreover, the specific herbicide used to control the volunteer conventional or transgenic soybean line is dependent upon the type of AAD transgenic corn seed (i.e. stacked traits or alone) being planted within the field and the trait possessed by the volunteer soybean line. For example an AAD-1 transgenic corn line that has been stacked with another herbicide tolerant trait such as PAT could be sprayed with a herbicide mixture containing glufosinate and a combination or single application of fluroxypyr, triclopyr, and/or 2,4-D; but only where the preceding volunteer plants do not contain PAT (or other glufosinate tolerant trait) and AAD-1.

The application of a given herbicide can be made before planting at pre-emergence/burndown or post-emergence after planting to control the volunteer conventional or transgenic soybean lines. Table 3 lists the herbicides to be used at the different stages of planting (pre-emergence or post-emergence) to control volunteer conventional or transgenic soybean. At or about a 1× Field Rate concentration of herbicide would be applied, as either a tank mix or alone, to the field for both pre-emergent and post-emergent volunteer control.

The control of conventional or transgenic soybean plants containing a herbicide tolerant expression cassette within a field of AAD transgenic corn (either stacked with other herbicide tolerant traits or alone) would be applicable for the control of a conventional or herbicide tolerant transgenic dicot plant (including, but not limited too; soybean, cotton, canola, flax, sunflower, legumes, alfalfa, peanut, and tomato) within a field being planted with a AAD transgenic monocot crop (including, but not limited too; corn, rice, sugar cane, switch grass, turf grass species, sorghum, barley, wheat, and oats, and durum). The example described above, in which volunteer conventional or transgenic herbicide tolerant soybean plants are controlled in a field planted with AAD transgenic corn, is illustrative of the invention and not intended to restrict the scope of this embodiment.

TABLE 1

Control of volunteer AAD-12 Soybean (alone or stacked with other HT traits) in HT Corn

| Previous year Soybean hybrid | Current year Corn hybrid being planted | Herbicides option - Burndown/PRE | Herbicides option - POST |
|---|---|---|---|
| | | Appl: alone and tank mixes | |
| AAD-12 | CL Corn<br>RR Corn<br>LL Corn<br>GAT<br>GAT + PAT<br>GAT + ALS<br>GAT + PAT + ALS<br>Dicamba<br>Dicamba + LL<br>Dicamba + RR<br>Dicamba + LL + RR | Glyphosate, glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks), glufosinate (only for use with LL corn single gene or stacks), Dicamba (only for use with Dicamba tolerant corn single gene or stacks) |
| AAD-12 + PAT | CL Corn<br>RR Corn<br>LL Corn<br>GAT<br>GAT + PAT<br>GAT + ALS<br>GAT + PAT + ALS<br>Dicamba<br>Dicamba + LL<br>Dicamba + RR<br>Dicamba + LL + RR | Glyphosate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks), Dicamba (only for use with Dicamba tolerant corn single gene or stacks) |
| AAD-12 + TIPS | CL Corn<br>RR Corn<br>LL Corn<br>GAT<br>GAT + PAT<br>GAT + ALS<br>GAT + PAT + ALS<br>Dicamba<br>Dicamba + LL<br>Dicamba + RR<br>Dicamba + LL + RR | Glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glufosinate (only for use with LL corn single gene or stacks), Dicamba (only for use with Dicamba tolerant corn single gene or stacks) |
| AAD-12 + AHAS | CL Corn<br>RR Corn<br>LL Corn<br>GAT<br>GAT + PAT<br>GAT + ALS<br>GAT + PAT + ALS<br>Dicamba<br>Dicamba + LL<br>Dicamba + RR<br>Dicamba + LL + RR | Glyphosate, glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks), glufosinate (only for use with LL corn single gene or stacks), Dicamba (only for use with Dicamba tolerant corn single gene or stacks) |
| AAD-12 + PAT + TIPS | CL Corn<br>RR Corn<br>LL Corn<br>GAT<br>GAT + PAT<br>GAT + ALS<br>GAT + PAT + ALS<br>Dicamba<br>Dicamba + LL<br>Dicamba + RR<br>Dicamba + LL + RR | Isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), Dicamba (only for use with Dicamba tolerant corn single gene or stacks) |
| AAD-12 + PAT + AHAS | CL Corn<br>RR Corn<br>LL Corn<br>GAT<br>GAT + PAT<br>GAT + ALS<br>GAT + PAT + ALS<br>Dicamba<br>Dicamba + LL<br>Dicamba + RR<br>Dicamba + LL + RR | Glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks), Dicamba (only for use with Dicamba tolerant corn single gene or stacks) |
| AAD-12 + GAT | CL Corn<br>RR Corn<br>LL Corn<br>GAT<br>GAT + PAT<br>GAT + ALS<br>GAT + PAT + ALS | Glufosinate, isoxaflutole, atrazine, alachlor, clopyralid, diflufenxopyr, mesotrione, isoxaflutole | Atrazine, clopyralid, diflufenxopyr, mesotrione, glufosinate (only for LL Corn traits), Dicamba (only for use with Dicamba tolerant corn single gene or stacks) |

TABLE 1-continued

Control of volunteer AAD-12 Soybean (alone or stacked with other HT traits) in HT Corn

| Previous year Soybean hybrid | Current year Corn hybrid being planted | Herbicides option - Burndown/PRE | Herbicides option - POST |
|---|---|---|---|
| | Dicamba | | |
| | Dicamba + LL | | |
| | Dicamba + RR | | |
| | Dicamba + LL + RR | | |

Gene and trait footnotes:

GT = any glyphosate specific tolerance trait including ROUNDUP READY (or GAT or other glyphosate-tolerant traits) (CP4), TIPS EPSPS (GA21, Glytol, DMMG), Athenix's EPSPS, GAT only without ALS, GOX, glyphosate decarboxylase, etc.

ALS = double mutant ALS gene insensitive to all ALS herbicide chemistries including IMI herbicides.

AAD-1 = Aryloxyalkanoate dioxygenase gene providing tolerance to all commercial phenoxy auxin and all aryloxyphenoxypropionate (fop) herbicides.

AAD-12 = Aryloxyalkanoate dioxygenase gene providing tolerance to phenoxyacetic auxin and pyridyloxyacetic auxin herbicides.

PAT = phosphinothricin acetyltransferase gene providing tolerance to glutamine synthetase inhibitors including, but not limited to, glufosinate. Similar phenotype is provided by genes such as BAR, DSM1, DSM2, et al.

AHAS = imidazolonine specific tolerance gene associated with point mutation at S623 of ALS gene (maize sequence) or equivalent amino acid in other spp (e.g., S653 in *Arabidopsis*).

RR = ROUNDUP READY trait, implies utility of CP4 gene as commercially deployed either alone or in combination with other genes but imparting glyphosate only tolerance.

CL = CLEARFIELD crops, tolerant by nontransgenic means. Primary tolerance is to imidazolinone class of ALS-inhibiting chemistry with some partial tolerance to specific other herbicides with this mode of action. Use of CL designation is intended to distinguish from transgenic use of the AHAS gene.

LL = LIBERTY LINK (glufosinate-tolerant) trait, implies utility of either PAT or BAR gene as commercially deployed either alone or in combination with other genes but imparting only tolerance to glutamine synthetase inhibitors such as glufosinate.

STS = designates resistance to sulfonylurea herbicide chemistry with use of ALS1 gene.

Herbicide footnotes:

IMI = any imidazolinone herbicide including, but not limited to, imazapyr, imazethapyr, imazamox, imazaquin.

DIMS = cyclohexanedione class of herbicides (dims) including, but not limited to, sethoxydim, clethodim, and for the purposes of this demonstration poinoxaden.

Fops = aryloxyphenoxypropionate herbicides (fops) including, but not limited to, quizalofop, haloxyfop, fenoxaprop, fluazifop, et al., their stereospecific isomers or racemic mixtures, and esters, acid, or salts thereof.

ALS inhibitors = any ALS inhibitor to the exclusion of IMI's for the sake of this demonstration (i.e., sulfonylureas, triazolopyrimidine sulfonanalides, sulfonylaminocarbonyltriazolinone).

HPPD = p-Hydroxyphenyl pyruvate dioxygenase inhibitor class of chemistry including but not limited to mesotrione, sulcotrione, isoxaflutole, and pyrazolynate.

MSMA and DSMA = herbicides from the organoarsenicals chemistry family.

N/A = No suitable options available postemergence.

TABLE 2

Control of volunteer AAD-12 Soybean (alone or stacked with other HT traits) in AAD-1 Corn

| Previous year Soybean hybrid | Current year Corn hybrid being planted | Herbicides option - Burndown/PRE | Herbicides option - POST |
|---|---|---|---|
| | Appl: alone and tank mixes | | |
| AAD-12 | AAD-1<br>AAD-1 + PAT<br>AAD-1 + GT<br>AAD-1 + GAT + ALS<br>AAD-1 + AHAS<br>AAD-1 + CL<br>AAD-1 + PAT + GT<br>AAD-1 + PAT + GAT + ALS<br>AAD-1 + PAT + AHAS | Glyphosate, glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks), glufosinate (only for use with LL corn single gene or stacks) |
| AAD-12 + PAT | AAD-1<br>AAD-1 + PAT<br>AAD-1 + GT<br>AAD-1 + GAT + ALS<br>AAD-1 + AHAS<br>AAD-1 + CL<br>AAD-1 + PAT + GT<br>AAD-1 + PAT + GAT + ALS<br>AAD-1 + PAT + AHAS | Glyphosate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks) |
| AAD-12 + TIPS | AAD-1<br>AAD-1 + PAT<br>AAD-1 + GT<br>AAD-1 + GAT + ALS<br>AAD-1 + AHAS<br>AAD-1 + CL<br>AAD-1 + PAT + GT<br>AAD-1 + PAT + GAT + ALS<br>AAD-1 + PAT + AHAS | Glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glufosinate (only for use with LL corn single gene or stacks) |
| AAD-12 + AHAS | AAD-1<br>AAD-1 + PAT<br>AAD-1 + GT<br>AAD-1 + GAT + ALS<br>AAD-1 + AHAS<br>AAD-1 + CL<br>AAD-1 + PAT + GT | Glyphosate, glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks), glufosinate (only for use with LL corn |

TABLE 2-continued

Control of volunteer AAD-12 Soybean (alone or stacked with other HT traits) in AAD-1 Corn

| Previous year Soybean hybrid | Current year Corn hybrid being planted | Herbicides option - Burndown/PRE | Herbicides option - POST |
|---|---|---|---|
|  | AAD-1 + PAT + GAT + ALS<br>AAD-1 + PAT + AHAS | restrictions) | single gene or stacks) |
| AAD-12 + PAT + TIPS | AAD-1<br>AAD-1 + PAT<br>AAD-1 + GT<br>AAD-1 + GAT + ALS<br>AAD-1 + AHAS<br>AAD-1 + CL<br>AAD-1 + PAT + GT<br>AAD-1 + PAT + GAT + ALS<br>AAD-1 + PAT + AHAS | Isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions) |
| AAD-12 + PAT + AHAS | AAD-1<br>AAD-1 + PAT<br>AAD-1 + GT<br>AAD-1 + GAT + ALS<br>AAD-1 + AHAS<br>AAD-1 + CL<br>AAD-1 + PAT + GT<br>AAD-1 + PAT + GAT + ALS<br>AAD-1 + PAT + AHAS | Glufosinate, isoxaflutole, atrazine, alachlor, clopyralid, diflufenxopyr, foramsulfuron, iodosulfuron, halosulfuron, mesotrione, isoxaflutole, nicosulfuron, rimsulfuron, prosulfuron, primisulfuron (need to be aware of planting restrictions) | Atrazine, clopyralid, diflufenxopyr, foramsulfuron, iodosulfuron, halosulfuron, mesotrione, nicosulfuron, rimsulfuron, prosulfuron, primisulfuron (need to be aware of planting restrictions), glyphosate (only for use with RR and GAT Corn single gene and stacks) |
| AAD-12 + GAT | AAD-1<br>AAD-1 + PAT<br>AAD-1 + GT<br>AAD-1 + GAT + ALS<br>AAD-1 + AHAS<br>AAD-1 + CL<br>AAD-1 + PAT + GT<br>AAD-1 + PAT + GAT + ALS<br>AAD-1 + PAT + AHAS | Glufosinate, isoxaflutole, atrazine, alachlor, clopyralid, diflufenxopyr, mesotrione, isoxaflutole | Atrazine, clopyralid, diflufenxopyr, mesotrione, glufosinate (only for LL Corn and AAD-1 + PAT based traits) |

Gene and trait footnotes:

GT = any glyphosate specific tolerance trait including ROUNDUP READY (or GAT or other glyphosate-tolerant traits) (CP4), TIPS EPSPS (GA21, Glytol, DMMG), Athenix's EPSPS, GAT only without ALS, GOX, glyphosate decarboxylase, etc.

ALS = double mutant ALS gene insensitive to all ALS herbicide chemistries including IMI herbicides.

AAD-1 = Aryloxyalkanoate dioxygenase gene providing tolerance to all commercial phenoxy auxin and all aryloxyphenoxypropionate (fop) herbicides.

AAD-12 = Aryloxyalkanoate dioxygenase gene providing tolerance to phenoxyacetic auxin and pyridyloxyacetic auxin herbicides.

PAT = phosphinothricin acetyltransferase gene providing tolerance to glutamine synthetase inhibitors including, but not limited to, glufosinate. Similar phenotype is provided by genes such as BAR, DSM1, DSM2, et al.

AHAS = imidazolinone specific tolerance gene associated with point mutation at S623 of ALS gene (maize sequence) or equivalent amino acid in other spp (e.g., S653 in *Arabidopsis*).

RR = ROUNDUP READY trait, implies utility of CP4 gene as commercially deployed either alone or in combination with other genes but imparting glyphosate only tolerance.

CL = CLEARFIELD crops, tolerant by nontransgenic means. Primary tolerance is to imidazolinone class of ALS-inhibiting chemistry with some partial tolerance to specific other herbicides with this mode of action. Use of CL designation is intended to distinguish from transgenic use of the AHAS gene.

LL = LIBERTY LINK (glufosinate-tolerant) trait, implies utility of either PAT or BAR gene as commercially deployed either alone or in combination with other genes but imparting only tolerance to glutamine synthetase inhibitors such as glufosinate.

STS = designates resistance to sulfonylurea herbicide chemistry with use of ALS1 gene.

Herbicide footnotes:

IMI = any imidazolinone herbicide including, but not limited to, imazapyr, imazethapyr, imazamox, imazaquin.

DIMS = cyclohexanedione class of herbicides (dims) including, but not limited to, sethoxydim, clethodim, and for the purposes of this demonstration poinoxaden.

Fops = aryloxyphenoxypropionate herbicides (fops) including, but not limited to, quizalofop, haloxyfop, fenoxaprop, fluazifop, et al., their stereospecific isomers or racemic mixtures, and esters, acid, or salts thereof.

ALS inhibitors = any ALS inhibitor to the exclusion of IMI's for the sake of this demonstration (i.e., sulfonylureas, triazolopyrimidine sulfonanalides, sulfonylaminocarbonyltriazolinone).

HPPD = p-Hydroxyphenyl pyruvate dioxygenase inhibitor class of chemistry including but not limited to mesotrione, sulcotrione, isoxaflutole, and pyrazolynate.

MSMA and DSMA = herbicides from the organoarsenicals chemistry family.

N/A = No suitable options available postemergence.

TABLE 3

Control of volunteer Soybean (alone or stacked with other Herbicide Tolerant traits) in AAD-1-based Corn

| Previous year Soybean hybrid | Current year Corn hybrid being planted | Herbicides option - Burndown/PRE | Herbicides option - POST |
|---|---|---|---|
| | | Appl: alone and tank mixes | |
| CL | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | Glyphosate, glufosinate, bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D, HPPD<br>2,4-D, HPPD, glufosinate<br>2,4-D, HPPD, glyphosate<br>2,4-D, HPPD<br>2,4-D, HPPD, glufosinate, glyphosate<br>2,4-D, HPPD, glufosinate<br>2,4-D, HPPD, glyphosate, ALS herbicides (sulfonylureas, triazolopyrimidine sulfonanalides, sulfobylamino carbonyl triazolinones) except imazaquin, |

TABLE 3-continued

Control of volunteer Soybean (alone or stacked with other Herbicide Tolerant traits) in AAD-1-based Corn

| Previous year Soybean hybrid | Current year Corn hybrid being planted | Herbicides option - Burndown/PRE | Herbicides option - POST |
|---|---|---|---|
| RR | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | Glufosinate, bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | imazpyr, imazamox, imazethapyr, chlorimuron, thifensulfuron<br>2,4-D, HPPD<br>2,4-D, HPPD, glufosinate<br>2,4-D, HPPD<br>2,4-D, HPPD<br>2,4-D, HPPD, glufosinate<br>2,4-D, HPPD, glufosinate<br>2,4-D, HPPD, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| LL | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | Glyphosate, bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D, HPPD<br>2,4-D, HPPD<br>2,4-D, HPPD, glyphosate<br>2,4-D, HPPD<br>2,4-D, HPPD, glyphosate<br>2,4-D, HPPD<br>2,4-D, HPPD, glyphosate, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| GAT | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | Glufosinate, bromoxynil, metribuzin, clomazone, flufenacet, s-metolachlor + fomesafen, pendimethalin | 2,4-D, HPPD<br>2,4-D, HPPD, glufosinate<br>2,4-D, HPPD<br>2,4-D, HPPD<br>2,4-D, HPPD, glufosinate<br>2,4-D, HPPD, glufosinate<br>2,4-D, HPPD |
| HPPD | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | Glyphosate, glufosinate, bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D<br>2,4-D, glufosinate<br>2,4-D, glyphosate<br>2,4-D<br>2,4-D, glufosinate, glyphosate<br>2,4-D, glufosinate<br>2,4-D, glyphosate, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| Dicamba | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | Glyphosate, glufosinate, bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D, HPPD<br>2,4-D, HPPD, glufosinate<br>2,4-D, HPPD, glyphosate<br>2,4-D, HPPD<br>2,4-D, HPPD, glufosinate, glyphosate<br>2,4-D, HPPD, glufosinate<br>2,4-D, HPPD, glyphosate, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| Dicamba + RR | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | glufosinate, bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D, HPPD<br>2,4-D, HPPD, glufosinate<br>2,4-D, HPPD<br>2,4-D, HPPD<br>2,4-D, HPPD, glufosinate<br>2,4-D, HPPD, glufosinate<br>2,4-D, HPPD, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| Dicamba + LL + RR | AAD-1<br>AAD-1 + PAT<br>AAD-1 + TIPS<br>AAD-1 + AHAS | bromoxynil, metribuzin, clomazone, flufenacet, s-metolachlor + fomesafen, pendimethalin, ALS herbicides not recommended for soybeans (need to | 2,4-D, HPPD<br>2,4-D, HPPD<br>2,4-D, HPPD<br>2,4-D, HPPD |

TABLE 3-continued

Control of volunteer Soybean (alone or stacked with other Herbicide Tolerant traits) in AAD-1-based Corn

| Previous year Soybean hybrid | Current year Corn hybrid being planted | Herbicides option - Burndown/PRE | Herbicides option - POST |
|---|---|---|---|
| | AAD-1 + PAT + TIPS<br>AAD-1 + PAT + AHAS<br>AAD-1 + GAT | be aware of planting restrictions): tribenuron, nicosulfuron, rimsulfuron | 2,4-D, HPPD<br>2,4-D, HPPD<br>2,4-D, HPPD, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| Dicamba + RR + HPPD | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | glufosinate, bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D<br>2,4-D, glufosinate<br>2,4-D<br>2,4-D<br>2,4-D, glufosinate<br>2,4-D, glufosinate<br>2,4-D, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |
| Dicamba + LL + RR + HPPD | AAD-1<br>AAD-1 + PAT<br>AAD-1 + TIPS<br>AAD-1 + AHAS<br>AAD-1 + PAT + TIPS<br>AAD-1 + PAT + AHAS<br>AAD-1 + GAT | bromoxynil, metribuzin, clomazone, flufenacet, s-metolachlor + fomesafen, pendimethalin, ALS herbicides not recommended for soybeans (need to be aware of planting restrictions): tribenuron, nicosulfuron, rimsulfuron | 2,4-D<br>2,4-D<br>2,4-D<br>2,4-D<br>2,4-D<br>2,4-D<br>2,4-D, ALS herbicides (sulfonylureas, triazolopyrimidine sulfonanalides, sulfobylamino carbonyl triazolinones) except imazaquin, imazpyr, imazamox, imazethapyr, chlorimuron, thifensulfuron |

Gene and trait footnotes:

GT = any glyphosate specific tolerance trait including ROUNDUP READY (or GAT or other glyphosate-tolerant traits) (CP4), TIPS EPSPS (GA21, Glytol, DMMG), Athenix's EPSPS, GAT only without ALS, GOX, glyphosate decarboxylase, etc.

ALS = double mutant ALS gene insensitive to all ALS herbicide chemistries including IMI herbicides.

AAD-1 = Aryloxyalkanoate dioxygenase gene providing tolerance to all commercial phenoxy auxin and all aryloxyphenoxypropionate (fop) herbicides.

AAD-12 = Aryloxyalkanoate dioxygenase gene providing tolerance to phenoxyacetic auxin and pyridyloxyacetic acid herbicides.

PAT = phosphinothricin acetyltransferase gene providing tolerance to glutamine synthetase inhibitors including, but not limited to, glufosinate. Similar phenotype is provided by genes such as BAR, DSM1, DSM2, et al.

AHAS = imidazolinone specific tolerance gene associated with point mutation at S623 of ALS gene (maize sequence) or equivalent amino acid in other spp (e.g., S653 in *Arabidopsis*).

RR = ROUNDUP READY trait, implies utility of CP4 gene as commercially deployed either alone or in combination with other genes but imparting glyphosate only tolerance.

CL = CLEARFIELD crops, tolerant by nontransgenic means. Primary tolerance is to imidazolinone class of ALS-inhibiting chemistry with some partial tolerance to specific other herbicides with this mode of action. Use of CL designation is intended to distinguish from transgenic use of the AHAS gene.

LL = LIBERTY LINK (glufosinate-tolerant) trait, implies utility of either PAT or BAR gene as commercially deployed either alone or in combination with other genes but imparting only tolerance to glutamine synthetase inhibitors such as glufosinate.

STS = designates resistance to sulfonylurea herbicide chemistry with use of ALS1 gene.

Herbicide footnotes:

IMI = any imidazolinone herbicide including, but not limited to, imazapyr, imazethapyr, imazamox, imazaquin.

DIMS = cyclohexanedione class of herbicides (dims) including, but not limited to, sethoxydim, clethodim, and for the purposes of this demonstration poinoxaden.

Fops = aryloxyphenoxypropionate herbicides (fops) including, but not limited to, quizalofop, haloxyfop, fenoxaprop, fluazifop, et al., their stereospecific isomers or racemic mixtures, and esters, acid, or salts thereof.

ALS inhibitors = any ALS inhibitor to the exclusion of IMI's for the sake of this demonstration (i.e., sulfonylureas, triazolopyrimidine sulfonanalides, sulfonylaminocarbonyltriazolinone).

HPPD = p-Hydroxyphenyl pyruvate dioxygenase inhibitor class of chemistry including but not limited to mesotrione, sulcotrione, isoxaflutole, and pyrazolynate.

MSMA and DSMA = herbicides from the organoarsenicals chemistry family.

N/A = No suitable options available postemergence.

The invention claimed is:

1. A method of controlling aryloxy alkanoate dioxygenase 12-containing dicot soybean volunteer plants in a field comprising monocot plants, wherein said volunteer plants are comprising Event DAS-68416-4, said Event comprising SEQ ID NO:1, wherein said method comprises applying a herbicide to said soybean volunteer plants, wherein said volunteer plants are susceptible to said herbicide, and said monocot plants are tolerant to said herbicide.

2. The method of claim 1, wherein said monocot plants are corn plants.

3. The method of claim 1, wherein said herbicide is selected from the group consisting of dicamba, clopyralid, and a triazine.

4. The method of claim 1, wherein said volunteer plants further comprise a glyphosate-tolerance gene, and said herbicide is glufosinate.

5. The method of claim 1, wherein said volunteer plants further comprise a glufosinate-tolerance gene, and said herbicide is glyphosate.

6. The method of claim 1, wherein said volunteer plants further comprise a glyphosate-tolerance gene, and said herbicide is selected from the group consisting of dicamba, clopyralid, and a triazine.

7. The method of claim 3, wherein said triazine herbicide is atrazine.

8. The method of claim 6, wherein said triazine herbicide is atrazine.

9. The method of claim 1, wherein said monocot plants comprise a glyphosate and/or a glufosinate-tolerance gene.

* * * * *

SEQUENCE LISTING

```
<160> NUMBER OF SEQ ID NOS: 1

<210> SEQ ID NO 1
<211> LENGTH: 10212
<212> TYPE: DNA
<213> ORGANISM: Artificial Sequence
<220> FEATURE:
<223> OTHER INFORMATION: Insert and Flanking squences for Soybean Event
      DAS-68416-4

<400> SEQUENCE: 1
```

```
ctgtcgttgg attcacagaa cattgacgcc agttttcact tcgttatctt tgaattcatt      60
aaaatcgaat ctctcaccta tacccccca tttttctaat ccatcataat caaaattcat      120
aaatgaatca gttaccatta ccataatacc tttttgaaaa tgagtttgaa taatcagtat     180
ctttagaaaa ctaattaaga aattaaataa aaaatattta tcatgaagat gagtgtaaga    240
aaaattatga aagtataac tttatacatt tctataaaat tatttttct tttaatttct      300 taattaatat cctaagtaaa tgagttaata tttatctttc aaaaattctt atagtcgcca    360
attaattttc ccatgcaatg acaacttgtc cgtattctac gtggtaggtt aggctacctg    420
ccgagacaaa ttgccttgag acaaattcaa tagagaaccc ttccaaggga ccattataaa    480
tagagaactt tcattaaccg ataagccaca ccctttcaat caaacacaaa cacttgaagt    540
actaagttag tgtgtttgag caaattaact atggcttcgt tttgttctag attgacaatt    600
tgtttggctc tgtttgtcct catatggggg agtgccaatg cacaactttc tacaaacttt    660
tactaccatt catgtccaaa cctcttctcc tctgtgaaat ccacagtgca atctgccata    720
tctaaggaga cccgcatggg tgcttctctc cttcgcttgt tcttccacga ttgctttgtc    780
aatgtaattt atttgcacct ctcccactt acatacaaat atgctaagct tacatatagc     840 tcctcttct accacttgca tgcatcatct aattttgttt gaaacaacac ttgttccttt     900
tattatacac atcatctttg ataaaatttt gtcgtgtgca acttttttt agtgtgttaa     960 tcagttctat gatgatacta ttagttaaga aattttaatg cacttaataa accatttta    1020 gtactttaac cgttcaatga tattatatat ttaaagataa taaatatttc tgcttttgtt   1080
tctatattag tgtagttaag aaccttctta cttcttagct agctaaatat taatgagtaa   1140
acattaacaa atgcagggat gtgatggttc aattctattg gatgacacat caagcttcac   1200
cggagagaag aacgcaaacc ccaacaggaa ctctgctcgt ggattcgagg ttattgacaa    1260
cattaaatca gccgtggaga aagtgtgtcc aggagttgtt tcctgcgcag atatccttgc    1320
catcgctgcc agagactctg ttcagattgt aagtggtcaa acaaccaaca aaaacacatt    1380
aaactaaatc attaaattgt acatatcaaa attaattacc aatttagtac cacacatgca    1440
attaaagaga cattttgttt gattttgatc aatatagctt ggaggcccta catggaatgt    1500
taaacttgga agaagagacg ctagaactgc tagccaatct gctgctaaca atggcatccc    1560
tgcacccact tcaaaccta accaactcat ctcaagattt agcgctcttg gactttccac    1620
caaggacttg gtcgccttgt ccggtacaaa acatatatca cataattttc caattaatta    1680
catttcaatc atatagtaaa atttctcaat taattaggaa catgagaaac ttatagtcac    1740
acgttctttt gttgaggaat attgcatggt ttaattttgc tttcattagg tggtcacaca    1800
attggacaag caaggtgcac aaacttcaga gcccgcatct acaacgagac caacatagaa    1860
accgcatttg caaggactag gcagcaaagc tgccctagaa catcagggtc aggggacaac    1920
aatctggcac cacttgatct tcaaactcca accagctttg acaactacta cttcaagaac    1980
ctcgttcaga agaagggtct cctccactct gatcagcaac tgttcaacgg tgggtccacc    2040
gactccattg tgcgtggcta cagcaccaac ccgggcacct tctcctctga tttcgccgcc    2100
gccatgatca agatgggaga cattagtcct ctcactggct ccaatggaga atcaggaag    2160 aattgtagaa ggattaacta atttgattca gtcttgaata ttaagggtcc tacacatacg   2220
caagcaattt aattgtgttt aataagttgt taaaacatgt tttggttgta ttttggattc    2280
ctagtgtagt ttcggtgatc aatgccgtct actttagtgt gttctacttc cctttatttt    2340
tgtttctttt ttacttttc cttaactata ttgtaggaaa aaaaaatcc tttatcaagc     2400
```

```
atttatcaag aacggagttt gcttttaat tttcccttca taacattcca tcagaattca    2460
gttttgcttt tgcttctaaa ttacgttcaa atcagggatg ataatcggtt aggtaatata    2520
tacagtaccc cttgcatagt cacgtttgaa aaatataatc atacttagtt cggtaacaat    2580
ttaaattatc attctcgtaa tcattagcta cttatgcact catatccgta tccgctactt    2640
gctcttgtcg taagtcaata aattaatata aaaaaatact taaaacttgt tacaactaaa    2700
ttaaaatttt attttttaaat cattcaagca ccagtcagca tcatcacacc aaaagttagg    2760
cccgaatagt ttgaaattag aaagctcgca attgaggtct acaggccaaa ttcgctctta    2820
gccgtacaat attactcacc ggatcctaac cggtgtgatc atgggccgcg attaaaaatc    2880
tcaattatat ttggtctaat ttagtttggt attgagtaaa acaaattcga accaaaccaa    2940
aatataaata tatagttttt atatatatgc ctttaagact ttttatagaa ttttctttaa    3000
aaaatatcta gaaatatttg cgactcttct ggcatgtaat atttcgttaa atatgaagtg    3060
ctccatttt attaactta aataattggt tgtacgatca ctttcttatc aagtgttact    3120
aaaatgcgtc aatctctttg ttcttccata ttcatatgtc aaaacctatc aaaattctta    3180
tatatctttt tcgaatttga agtgaaattt cgataattta aaattaaata gaacatatca    3240
ttatttaggt atcatattga tttttatact taattactaa atttggttaa ctttgaaagt    3300
gtacatcaac gaaaaattag tcaaacgact aaaataaata aatatcatgt gttattaaga    3360
aaattctcct ataagaatat tttaatagat catatgtttg taaaaaaaat taattttttac    3420
taacacatat atttacttat caaaaatttg acaaagtaag attaaaataa tattcatcta    3480
acaaaaaaaa aaccagaaaa tgctgaaaac ccggcaaaac cgaaccaatc caaaccgata    3540
tagttggttt ggtttgattt tgatataaac cgaccaact cggtccattt gcacccctaa    3600
tcataatagc tttaatattt caagatatta ttaagttaac gttgtcaata tcctggaaat    3660
tttgcaaaat gaatcaagcc tatatggctg taatatgaat ttaaaagcag ctcgatgtgg    3720
tggtaatatg taatttactt gattctaaaa aaatatccca agtattaata atttctgcta    3780
ggaagaaggt tagctacgat ttacagcaaa gccagaatac aatgaaccat aaagtgattg    3840
aagctcgaaa tatacgaagg aacaaatatt tttaaaaaaa tacgcaatga cttggaacaa    3900
aagaaagtga tatatttttt gttcttaaac aagcatcccc tctaaagaat ggcagttttc    3960
ctttgcatgt aactattatg ctcccttcgt tacaaaaatt ttggactact attgggaact    4020
tcttctgaaa atagtggcca ccgcttaatt aaggcgcgcc atgcccgggc aagcggccgc    4080
acaagtttgt acaaaaaagc aggctccgcg gtgactgact gaaaagcttg tcgacctgca    4140
ggtcaacgga tcaggatatt cttgtttaag atgttgaact ctatggaggt ttgtatgaac    4200
tgatgatcta ggaccggata agttcccttc ttcatagcga acttattcaa agaatgtttt    4260
gtgtatcatt cttgttacat tgttattaat gaaaaatat tattggtcat tggactgaac    4320
acgagtgtta aatatggacc aggccccaaa taagatccat tgatatatga attaaataac    4380
aagaataaat cgagtcacca aaccacttgc cttttttaac gagacttgtt caccaacttg    4440
atacaaaagt cattatccta tgcaaatcaa taatcataca aaaatatcca ataacactaa    4500
aaaattaaaa gaaatggata atttcacaat atgttatacg ataagaagt tacttttcca    4560
agaaattcac tgatttata agcccacttg cattagataa atggcaaaaa aaaacaaaaa    4620
ggaaaagaaa taaagcacga agaattctag aaaatacgaa atacgcttca atgcagtggg    4680
acccacggtt caattattgc caattttcag ctccaccgta tatttaaaaa ataaaacgat    4740
```

-continued

```
aatgctaaaa aaatataaat cgtaacgatc gttaaatctc aacggctgga tcttatgacg    4800
accgttagaa attgtggttg tcgacgagtc agtaataaac ggcgtcaaag tggttgcagc    4860
cggcacacac gagtcgtgtt tatcaactca aagcacaaat acttttcctc aacctaaaaa    4920
taaggcaatt agccaaaaac aactttgcgt gtaaacaacg ctcaatacac gtgtcatttt    4980
attattagct attgcttcac cgccttagct ttctcgtgac ctagtcgtcc tcgtcttttc    5040
ttcttcttct tctataaaac aatacccaaa gcttcttctt cacaattcag atttcaattt    5100
ctcaaaatct taaaaacttt ctctcaattc tctctaccgt gatcaaggta aatttctgtg    5160
ttccttattc tctcaaaatc ttcgattttg ttttcgttcg atcccaattt cgtatatgtt    5220
ctttggttta gattctgtta atcttagatc gaagacgatt ttctgggttt gatcgttaga    5280
tatcatctta attctcgatt agggtttcat aaatatcatc cgatttgttc aaataatttg    5340
agttttgtcg aataattact cttcgatttg tgatttctat ctagatctgg tgttagtttc    5400
tagtttgtgc gatcgaattt gtcgattaat ctgagttttt ctgattaaca gagatctcca    5460
tggctcagac cactctccaa atcacaccca ctggtgccac cttgggtgcc acagtcactg    5520
gtgttcacct tgccacactt gacgatgctg gtttcgctgc cctccatgca gcctggcttc    5580
aacatgcact cttgatcttc cctgggcaac acctcagcaa tgaccaacag attacctttg    5640
ctaaacgctt tggagcaatt gagaggattg gcggaggtga cattgttgcc atatccaatg    5700
tcaaggcaga tggcacagtg cgccagcact ctcctgctga gtgggatgac atgatgaagg    5760
tcattgtggg caacatggcc tggcacgccg actcaaccta catgccagtc atggctcaag    5820
gagctgtgtt cagcgcagaa gttgtcccag cagttggggg cagaacctgc tttgctgaca    5880
tgagggcagc ctacgatgcc cttgatgagg caacccgtgc tcttgttcac caaaggtctg    5940
ctcgtcactc ccttgtgtat tctcagagca agttgggaca tgtccaacag gccgggtcag    6000
cctacatagg ttatggcatg gacaccactg caactcctct cagaccattg gtcaaggtgc    6060
atcctgagac tggaaggccc agcctcttga tcggccgcca tgcccatgcc atccctggca    6120
tggatgcagc tgaatcagag cgcttccttg aaggacttgt tgactgggcc tgccaggctc    6180
ccagagtcca tgctcaccaa tgggctgctg agatgtggt tgtgtgggac aaccgctgtt    6240
tgctccaccg tgctgagccc tgggatttca gttgccacg tgtgatgtgg cactccagac    6300
tcgctggacg cccagaaact gagggtgctg ccttggtttg agtagttagc ttaatcacct    6360
agagctcggt caccagcata atttttatta atgtactaaa ttactgtttt gttaaatgca    6420
attttgcttt ctcgggattt taatatcaaa atctatttag aaatacacaa tattttgttg    6480
caggcttgct ggagaatcga tctgctatca taaaaattac aaaaaaattt tatttgcctc    6540 aattattttta ggattggtat taaggacgct taaattattt gtcgggtcac tacgcatcat    6600
tgtgattgag aagatcagcg atacgaaata ttcgtagtac tatcgataat ttatttgaaa    6660
attcataaga aaagcaaacg ttacatgaat tgatgaaaca atacaaagac agataaagcc    6720
acgcacattt aggatattgg ccgagattac tgaatattga gtaagatcac ggaatttctg    6780
acaggagcat gtcttcaatt cagcccaaat ggcagttgaa atactcaaac cgccccatat    6840
gcaggagcgg atcattcatt gtttgtttgg ttgcctttgc caacatggga gtccaaggtt    6900
gcggccgcgc gccgacccag ctttcttgta caaagtggtt gcggccgctt aattaaattt    6960
aaatgcccgg gcgtttaaac gcggccgctt aattaaggcc ggcctgcagc aaacccagaa    7020
ggtaattatc caagatgtag catcaagaat ccaatgttta cggaaaaaac tatgaagta    7080 ttatgtaagc tcagcaagaa gcagatcaat atgcggcaca tatgcaacct atgttcaaaa    7140
```

```
atgaagaatg tacagataca agatcctata ctgccagaat acgaagaaga atacgtagaa    7200
attgaaaaag aagaaccagg cgaagaaaag aatcttgaag acgtaagcac tgacgacaac    7260
aatgaaaaga agaagataag gtcggtgatt gtgaaagaga catagaggac acatgtaagg    7320
tggaaaatgt aagggcggaa agtaaccttc tcacaaagga atcttatccc ccactactta    7380
tccttttata ttttccgtg tcattttgc ccttgagttt tcctatataa ggaaccaagt     7440
tcggcatttg tgaaaacaag aaaaaatttg gtgtaagcta ttttctttga agtactgagg    7500
atacaacttc agagaaattt gtaagtttgt agatctccat gtctccggag aggagaccag    7560
ttgagattag gccagctaca gcagctgata tggccgcggt ttgtgatatc gttaaccatt    7620
acattgagac gtctacagtg aactttagga cagagccaca acaccacaa gagtggattg     7680
atgatctaga gaggttgcaa gatagatacc cttggttggt tgctgaggtt gagggtgttg    7740
tggctggtat tgcttacgct gggccctgga aggctaggaa cgcttacgat tggacagttg    7800
agagtactgt ttacgtgtca cataggcatc aaaggttggg cctaggatcc acattgtaca    7860
cacatttgct taagtctatg gaggcgcaag gttttaagtc tgtggttgct gttataggcc    7920
ttccaaacga tccatctgtt aggttgcatg aggctttggg atacacagcc cggggtacat    7980
tgcgcgcagc tggatacaag catggtggat ggcatgatgt tggttttgg caaagggatt     8040
ttgagttgcc agctcctcca aggccagtta ggccagttac ccagatctga ggtaccctga    8100
gcttgagctt atgagcttat gagcttagag ctcggatcca ctagtaacgg ccgccagtgt    8160
gctggaattc gcccttgact agataggcgc ccagatcggc ggcaatagct tcttagcgcc    8220
atcccgggtt gatcctatct gtgttgaaat agttgcggtg ggcaaggctc tctttcagaa    8280
agacaggcgg ccaaaggaac ccaaggtgag gtgggctatg gctctcagtt ccttgtggaa    8340
gcgcttggtc taaggtgcag aggtgttagc gggatgaagc aaaagtgtcc gattgtaaca    8400
agatatgttg atcctacgta aggatattaa agtatgtatt catcactaat ataatcagtg    8460
tattccaata tgtactacga tttccaatgt ctttattgtc gccgtatgta atcggcgtca    8520
caaaataatc cccggtgact ttcttttaat ccaggatgaa ataatatgtt attataattt    8580
ttgcgatttg gtccgttata ggaattgaag tgtgcttgcg gtcgccacca ctcccatttc    8640
ataattttac atgtatttga aaaataaaaa tttatggtat tcaatttaaa cacgtatact    8700
tgtaaagaat gatatcttga aagaaatata gtttaaatat ttattgataa aataacaagt    8760
caggtattat agtccaagca aaaacataaa tttattgatg caagtttaaa ttcagaaata    8820
tttcaataac tgattatatc agctggtaca ttgccgtaga tgaaagactg agtgcgatat    8880
tatggtgtaa tacatagcgg ccgggtttct agtcaccggt taggatccgt ttaaactcga    8940
ggctagcgca tgcacataga cacacacatc atctcattga tgcttggtaa taattgtcat    9000
tagattgttt ttatgcatag atgcactcga aatcagccaa ttttagacaa gtatcaaacg    9060
gatgtgactt cagtacatta aaaacgtccg caatgtgtta ttaagttgtc taagcgtcaa    9120
tattttaatt cttaacaatc aatattttaa ttcttaaact ttattaaatc taacaataaa    9180
ctgtaagaac taattcttaa acttcaataa acaatactgc gttttagtaa ttaaattaat    9240
aatatataga tatagatata taatttgtca acatattctt acctattttt ccattgaaat    9300
atgttagcaa gttcaaaaaa agttttgaca aaaaactcta ctatcttttg tttcatttac    9360
tttatgtgag ggatataata gtaatataac atttagttta tttaaagaaa ataaaaaagt    9420
taatttctct ttctgccact gatactctat ggtggagaga tccgatgcag tggtggagcc    9480
```

```
tggcctcgac acataagtgt gacgacgcag ctgttgaaga gatctgattc gacggtgggg    9540
taatgcatgg tggttgacag gttgatgggt ggagaagacg taattgctac cgccgtcaac    9600
ggaggaagga gcaaagatgt ctcgtatgtg aaaattatgc ggttgagatg ccgtttcatt    9660
ccctttaaaa aaatcccttg atggttgcaa tgcaaattaa aaattgaaaa aataattaat    9720
tgttcaaatt aaagatttag catgaaaaaa aaaacactta attgtgccca tgactccatg    9780
acctgcgtaa cttgggaagg aaaggaattt ttttgctaaa ggaaggcatg ggaagatgag    9840
agaggagaga gaatcagtgg aagtgagaga aattaacttt ttgttttta aaaactaaat     9900 attatattac tattatatat atatatatat atatataaaa gattttttag ctggattctt    9960
gatataaaaa atttctcacc atatttatta ttatatattt ttttggagat ctcaaaaaag   10020
gaagttggat ttcttctcaa taactctaaa aaattattcc tatttcaaaa aatatttttt   10080
atgtctttct ctaattgatg aataatatct atttaagtat attttattgt gaaatccaca   10140
aaagtgactg ataaatctaa tttaggatct accattagag aaaaataaat aaattcttat   10200
attatatgtg at                                                       10212
```